United States Patent [19]

Zaiger et al.

[11] Patent Number: Plant 7,532

[45] Date of Patent: May 28, 1991

[54] PEACH TREE ("SUGAR LADY")

[76] Inventors: Chris F. Zaiger, 537 Rosemore Ave.; Gary N. Zaiger, 1907 Elm Ave.; Leith M. Gardner, 1207 Grimes Ave.; Grant G. Zaiger, 2121 Elm Ave., all of Modesto, Calif. 95351

[21] Appl. No.: 377,905

[22] Filed: Jul. 10, 1989

[51] Int. Cl.[5] ..... A01H 5/00

[52] U.S. Cl. ..... Plt./42

[58] Field of Search ..... Plt. 42

[56] References Cited

U.S. PATENT DOCUMENTS

| | | | |
|---|---|---|---|
| P.P. 1,353 | 2/1955 | Fujihara | Plt. 42 |
| P.P. 5,821 | 12/1986 | Zaiger et al. | Plt. 42 |
| P.P. 6,409 | 11/1988 | Zaiger et al. | Plt. 42 |
| P.P. 7,065 | 12/1989 | Zaiger et al. | Plt. 42 |

*Primary Examiner*—Howard J. Locker

[57] ABSTRACT

A new and distinct variety of peach tree with the following unique combination of features which are outstanding in a new variety:

1. Ability to produce white flesh fruit with an attractive red skin color.
2. Fruit with firmer flesh than most other varieties of white flesh peaches.
3. Fruit with sub-acid, mild, sweet, delicate flavor with very good eating quality.
4. A regular and productive bearer of fruit.
5. Large, nearly uniform size of fruit throughout the tree.
6. Uniform ripening of fruit.

1 Drawing Sheet

ORIGIN OF THE VARIETY

The new variety of peach tree was originated by us in the experimental orchard located at Modesto. Calif. from a cross between two selected seedlings. The female parent was a second generation seedling selection from a cross between O'Henry Peach (U.S. Plant Pat. No. 2,964) and Giant Babcock Peach (U.S. Pat. No. 1,353). The pollen parent was a selected seedling from a group of seedlings grown from open pollinated May Grand Nectarine (U.S. Plant Pat. No. 2,794) seed. We grew and maintained a large group of seedlings under close observation and the present variety exhibited the desirable characteristics described above and was selected for asexual reproduction and commercialization.

ASEXUAL REPRODUCTION OF THE VARIETY

Asexual propagation of the new and distinct variety of peach tree was performed by budding in the experimental orchard located at Modesto, Calif. and shows that such reproduction runs true to form and said characteristics are established and transmitted through succeeding propagations.

SUMMARY OF THE VARIETY

The new and distinct variety of peach tree is of large, vigorous, upright growth and is a regular and productive bearer of large, white flesh, freestone fruit with an attractive red skin color. The flesh is firmer than most white flesh varieties and has a sub-acid, mild, sweet, delicate flavor with very good eating quality. In comparison to the white flesh parent Giant Babcock Peach (U.S. Plant Pat. No. 1,353) the fruit of the new variety has firmer flesh with greater handling and shipping quality, and allows picking of the fruit at a more mature stage. The fruit of the new variety also has less apexal point than Giant Babcock, a greater degree of attractive red skin color, more uniform size of fruit throughout the tree and matures approximately 21 days earlier. Although no detailed studies have been made, the new variety is apparently tolerant to many types of soil and a wide range of climatic conditions, much like its paternal parent.

PHOTOGRAPHS OF THE VARIETY

The accompanying color photographs show typical specimens of the foliage and fruit of the new variety, with the upper and lower surface of the leaves being illustrated, an exterior and sectional view of the fruit depicted with the stone remaining in place. The photographic illustrations were taken shortly after being picked at maturity (firm ripe) and the colors are as nearly true as reasonably possible in a color representation of this type.

DESCRIPTION OF THE VARIETY

The following is a detailed botanical description of the new variety of peach tree, its fruit, flowers and foliage, as based on observations of the variety grown at Modesto, Calif., with color terminology (except those in common color terms) in accordance with Reinhold Color Atlas., by A. Korneruf and J. H. Wanscher.

Tree;
- *Size.*—Large.
- *Vigor.*—Vigorous.
- *Form.*—Upright.
- *Productivity.*—Productive.
- *Bearer.*—Regular.
- *Density.*—Medium dense.

Trunk:
- *Size.*—Medium stocky.
- *Texture.*—Medium shaggy.
- *Color.*—Brown to dull brown.

Branches:
- *Size.*—Medium.
- *Texture.*—Smooth to medium rough.
- *Lenticels.*—Medium size. Medium quantity.

Leaves:
- *Size.*—Large. Average length — 6¾" to 7¼" Average width — 1½" to 1⅝".
- *Form.*—Lanceolate.
- *Thickness.*—Medium.
- *Margin.*—Crenate.
- *Petiole.*—Average length — ⅝". Average width — 1/16".
- *Glands.*—Reniform. Number range 2 to 6. Average number 4. Positioned on lower part of leaf blade and upper portion of petiole.
- *Color.*—Upper surface — green to deep green (27-E-7) to (27-F-8). Lower surface — green to grayish green (28-E-7) to (28-E-8).

Flower buds:
- *Size.*—Large.
- *Form.*—Plump.
- *Pubescence.*—Pubescent.

Flowers:
- *Size.*—Large — showy.
- *Pollen.*—Present.
- *Color.*—Pink.
- *Blooming period.*—Feb. 26, 1987 to Mar. 5, 1987. Varies slightly with climatic conditions.

Fruit:
- *Maturity when described.*—Firm ripe.
- *Date of first picking.*—Jun. 23, 1987.
- *Date of last picking.*—Jun. 28, 1987.
- *Size.*—Large. Average diameter axially to 2⅞" to 3⅛". Average transversely in suture plane 2⅞" to 3⅛".
- *Form.*—Globose nearly symmetrical slightly flattened at stem end.
- *Suture.*—Shallow extends from base to apex.
- *Ventral surface.*—Nearly rounded.
- *Base.*—Retuse.
- *Cavity.*—Nearly rounded, only slightly elongated in suture plane. Average depth — ⅝" Average breadth — 1".
- *Apex.*—Nearly rounded, only slight pistil point.

Skin:
- *Thickness.*—Medium.
- *Texture.*—Medium — tenacious to flesh when firm ripe. Free when soft ripe.
- *Tendency to crack.*—None.
- Down.—Moderate. Medium length.
- *Color.*—Yellowish white ground color (3-A-2) to (3-A-5). Overspread with light red blush (9-A-5) to currant red (9-B-8).

Flesh:
- *Texture.*—Firm.
- *Fibers.*—Few, tender.
- *Ripens.*—Evenly.
- *Flavor.*—Sub-acid, mild, delicately sweet.
- *Juice.*—Moderate.
- *Amygdalin.*—Undetected.
- *Aroma.*—Moderate.
- *Eating quality.*—Very good.
- *Color.*—Varies from white to pale yellowish white (2-A-1) to (2-A-2). Pit cavity and area around pit cavity ranges from red to light red (10-B-8) to (10-A-7).

Stone:
- *Type.*—Freestone.
- *Size.*—Large. Average length — 1¾". Average breadth — 1 1/16". Average thickness — ¾".
- *Form.*—Ovoid.
- *Base.*—Mostly rounded, some straight.
- *Apex.*—Acuminate.
- *Sides.*—Equal to unequal.
- *Surface.*—Irregularly furrowed toward apex, pitted toward base.
- *Tendency to split.*—Very slight.
- *Color.*—Brown to reddish brown (8-E-8) to (9-D-8).

Use: Dessert.
- *Market.*—Local and long distance.

Keeping quality: Good.

Shipping quality: Good.

The present variety of peach tree, its leaves and fruit herein described are as grown under the ecological conditions prevailing at Modesto, Calif. The variety may vary in slight detail due to different climatic, soil conditions and cultural practices under which the variety may be grown.

We claim:

1. A new and distinct variety of peach tree as illustrated and described, characterized by its large size, vigorous, upright growth and a regular and productive bearer of large, firm, white flesh, freestone fruit that have a sub-acid, mild, sweet delicate flavor with very good eating quality; the fruit is further characterized in comparison to the white flesh Giant Babcock Peach (U.S. Plant Pat. No. 1,353) by having a higher degree of red skin color, firmer flesh with greater shipping and storage quality and maturing approximately 21 days earlier.

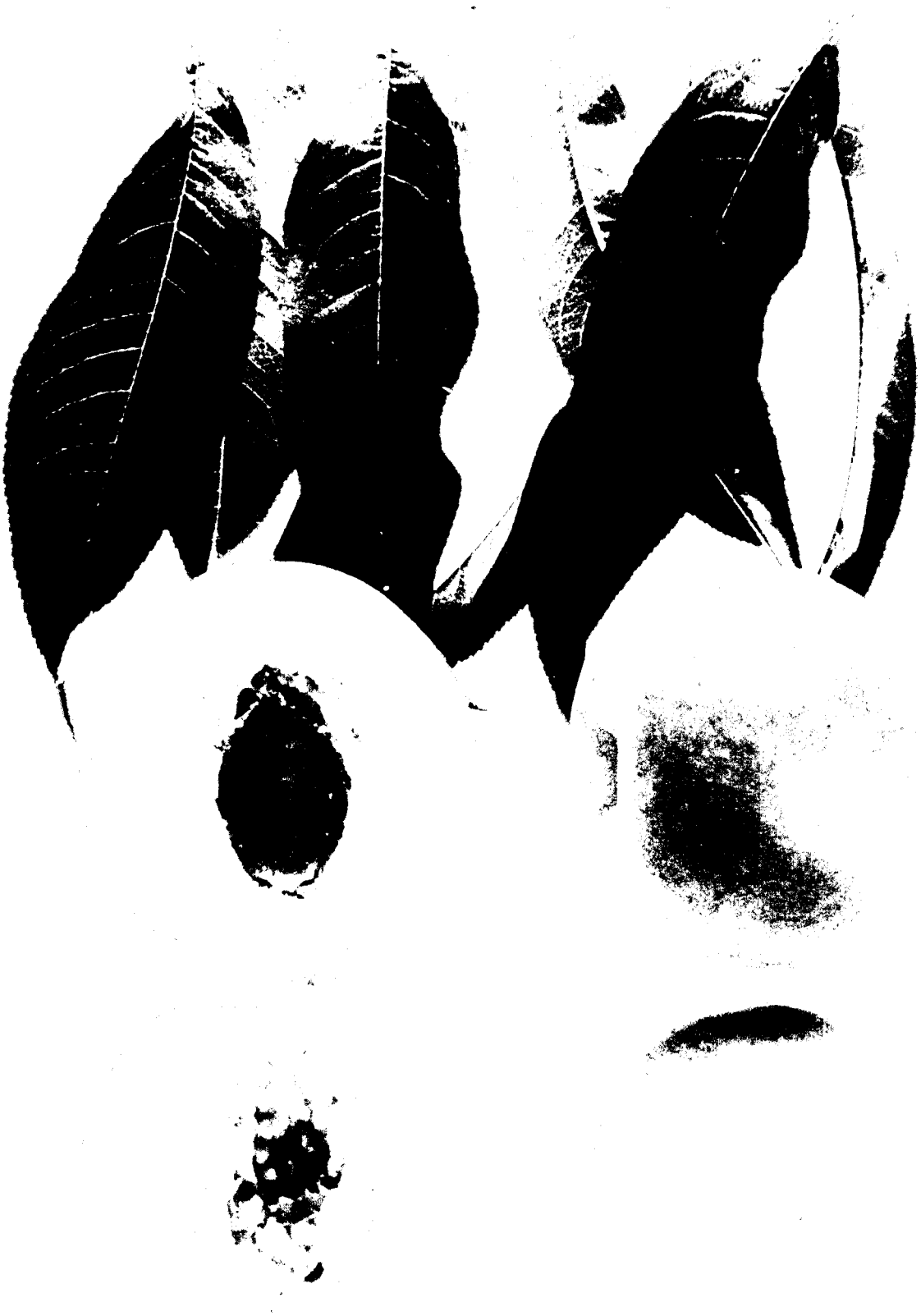

* * * * *